United States Patent [19]

Chen

[11] Patent Number: 5,439,825
[45] Date of Patent: Aug. 8, 1995

[54] ANALYSIS OF HEMOGLOBIN VARIANTS BY CAPILLARY ZONE ELECTROPHORESIS

[75] Inventor: Fu-Tai A. Chen, Brea, Calif.

[73] Assignee: Beckman Instruments, Inc., Fullerton, Calif.

[21] Appl. No.: 988,576

[22] Filed: Dec. 10, 1992

Related U.S. Application Data

[62] Division of Ser. No. 870,531, Apr. 17, 1992, Pat. No. 5,202,006.

[51] Int. Cl.⁶ ............................................. G01N 33/00
[52] U.S. Cl. ........................................ 436/18; 436/66; 436/500; 436/516; 436/536; 435/816; 544/302; 544/303
[58] Field of Search ........................... 435/7.4, 12, 816; 436/18, 500, 66, 516, 536; 544/302, 303

[56] References Cited

U.S. PATENT DOCUMENTS

| | | | |
|---|---|---|---|
| 3,607,695 | 9/1971 | Schneider | 436/66 X |
| 3,615,222 | 10/1971 | Mead | 436/500 X |
| 3,721,528 | 3/1973 | Mead et al. | 436/500 X |
| 3,875,005 | 4/1975 | Belloc et al. | 435/816 X |
| 3,904,627 | 9/1975 | Vida et al. | 544/302 X |
| 3,919,232 | 11/1975 | Barer | 544/303 X |
| 3,920,656 | 11/1975 | Vida | 544/302 X |
| 3,920,686 | 11/1975 | Samour | 544/302 X |
| 3,947,564 | 3/1976 | Shannon et al. | 436/500 X |
| 3,951,776 | 4/1976 | Eibl et al. | 436/516 X |
| 4,029,662 | 6/1977 | Vida | 544/302 X |
| 4,036,823 | 7/1977 | Soares | 436/527 X |
| 4,046,894 | 9/1977 | Gamour et al. | 544/302 X |
| 4,158,547 | 6/1979 | Rousseau et al. | 436/500 X |
| 4,194,063 | 3/1980 | Frank et al. | 435/12 |
| 4,205,952 | 6/1980 | Cais | 436/536 X |
| 4,209,372 | 6/1980 | Bluestein et al. | 204/180 G |
| 4,249,005 | 2/1981 | Samour et al. | 544/302 |
| 4,273,867 | 6/1981 | Lin et al. | 435/7.4 |
| 4,298,592 | 11/1981 | Lin et al. | 435/7.4 X |
| 4,696,958 | 9/1987 | Gurske | 524/21 |

FOREIGN PATENT DOCUMENTS

| | | |
|---|---|---|
| 0122742 | 10/1984 | European Pat. Off. . |
| 3229938 | 9/1983 | Germany . |

Primary Examiner—James C. Housel
Assistant Examiner—Harold Y. Pyon
Attorney, Agent, or Firm—William H. May; Arnold Grant; Sheldon & Mak

[57] ABSTRACT

Disclosed herein are buffers and methodologies for the capillary zone electrophoretic analysis of hemoglobin and the variants of hemoglobin. In a particularly preferred embodiment, the buffer comprises at least about 100 mM of barbituric acid, derivatives of barbituric acid, combinations of barbituric acid and derivatives of barbituric acid, and combinations of the derivatives of barbituric acid, and has a pH of at least about 8.0.

8 Claims, 4 Drawing Sheets

ANALYSIS OF HEMOGLOBIN VARIANTS BY CAPILLARY ZONE ELECTROPHORESIS

This is a division of application Ser. No. 07/870,531 filed Apr. 17, 1992 now U.S. Pat. No. 5,202,006.

FIELD OF THE INVENTION

The present invention is generally directed to the analysis of samples in general, and more specifically to the analysis of samples utilizing capillary electrophoretic techniques. In a particularly preferred embodiment, the invention is directed to the analysis of clinical samples for hemoglobin variants by capillary electrophoretic techniques.

BACKGROUND OF THE INVENTION

Normal human hemoglobin (or "haemoglobin") is a protein having a molecular weight of approximately 68,000 Daltons. Hemoglobin comprises four globin chains, each with a heme group attached; two of the globin chains in normal hemoglobin are referred to as "$\alpha$(alpha)-chains", while the other two non-$\alpha$ chains are selected from $\beta$(beta), $\gamma$(gamma) or $\delta$(delta) chains. The resulting four chain molecule can be referred to as a "tetramer". Typically, the hemoglobin types are designated based upon these chains, i.e. $\alpha_2\beta_2$ or $\alpha_2\delta_2$ indicating two $\alpha$ chains, two $\beta$ chains and two $\alpha$ chains, two $\delta$ chains, respectively. The hemoglobins present in a normal adult are Hemoglobin A ($\alpha_2\beta_2$), which comprises about 97% of the total hemoglobin, Hemoglobin $A_2$ ($\alpha_2\delta_2$), and Hemoglobin F($\alpha_2\delta_2$), which comprise the remaining 3%.

The orientation of these four chains is such that the hemoglobin moiety comprises a cleft, or "pocket", on its exterior. This cleft contains the site of oxygen uptake and release, which is the principal function of hemoglobin. It is the interaction of the four globin chains which allows for alteration in spatial relationships between portions of the molecule, and this facilitates the uptake or release of oxygen. Abnormalities in the structure of the hemoglobin molecule can result in an inability to, e.g., properly regulate the uptake and release of oxygen.

The $\alpha$ chains comprise 141 amino acids and the non-$\alpha$ chains comprise 146 amino acids. The exact type, number and precise sequence of these amino acids is characteristic for each type of globin chain; any alteration in the sequences gives rise to an abnormal globin chain, resulting in the production of abnormal hemoglobin. Abnormal hemoglobins are part of a group of inherited disorders collectively referred to as the "hemoglobinopathies."

Hemoglobinopathies are the result of defective synthesis of the globin chains which form the hemoglobin molecule. Such a defect can occur in at least two ways: (1) synthesis of a structurally abnormal globin chain at the genetic level, and (2) decrease production of a structurally normal globin chain whereby the $\alpha$ and non-$\alpha$ chains are synthesized in unequal quantities, and the resultant imbalanced chain production causes an inadequate production of the normal hemoglobin, which forms an unstable tetramer. Conditions which arise from such imbalanced chain production are referred to as the "thalassemia syndromes."

With reference to structural defects, approximately 400 structural abnormalities of the globin chain have been described. The vast majority of these provide neither clinical nor hematologic manifestations. These hemoglobin structural variants are due principally to point mutations, insertions or deletions of the nucleotides encoding the globin genes, or deletions or fusion of these genes. Hemoglobin S (HbS) is by far the most important abnormal hemoglobin variant in terms of clinical significance. Individuals having two genes for HbS ("homozygous" for HbS) have sickle-cell anemia and will be at risk of severe life threatening crises. The phrase "sickle-cell" is derived from the observed sickle-shaped red blood cells characteristic of HbS. Individuals with sickle cell anemia can experience painful sickling crises when the sickle cells cause blockage of the arteries, resulting in vasa-occlusion and tissue infarctions.

With reference to the second type of hemoglobinopathy, the thalassemia syndromes, a reduction as $\alpha$-chain synthesis results in a condition referred to an "$\alpha$-thalassemia". Alpha-thalassemia is considered to be the most common genetic disorder in humans. Clinical expressions of $\alpha$-thalassemia range from none to very severe; these expressions can be determined by analysis of the hemoglobins. I.e., individuals having three deleted $\alpha$-genes typically evidence an increase in Hemoglobin F and the appearance of Hemoglobin H. Beta-thalassemias have similar varying degrees of clinical expressions and these can also be determined by analysis of the hemoglobins, i.e. for certain $\beta$-thalassemias, no Hemoglobin A is present, while for $\delta\beta$-thalassemia, Hemoglobin F is characteristically increased to 5-20% of total hemoglobin.

Many of the hemoglobinopathies are race specific. For example, about 30% of African-Americans and persons of southeast Asia origin have a gene for $\alpha$-thalassemia. Beta-thalassemia occurs frequently in Mediterranean and Asian individuals.

Screening for the presence of abnormal hemoglobins is typically conducted with the intent of detecting both clinically significant and clinically silent abnormal hemoglobins. For example, it is essential to screen any person of non-Northern European origin who is undergoing an anaesthetic procedure for the presence of HbS. This is because the presence of HbS indicates a possible inability to properly regulate the uptake of oxygen such that appropriate anaesthetic procedures are utilized. Such screening is also useful in genetic counseling. Individuals who, for example, are "heterozygous" for the HbS gene (one gene for HbS; sickle cell carrier) have sickle cell traits and can experience no clinical manifestations. However, when two such individuals pro-create, their offspring have a 50% chance of inheriting both HbS genes, i.e. a 50% chance of being heterozygous for HbS and having sickle cell anemia.

There are currently two principal approaches utilized for the separation and detection of hemoglobin variants: a) slab-gel electrophoresis and b) isoelectric focusing. Both protocols are based upon the ability of hemoglobin variants to be separated from each other due to the difference in electrophoretic mobilities of such variants. The amino acid differences in the composition of hemoglobin variants are responsible for the differences in electrical charge, and this produces the difference in electrophoretic mobility. Under the influence of a charged field, all of the variants will move toward a designated charge opposite to the charge of the variants; those having a lower electrophoretic mobility will move slower than, and hence be separated from, those having a (relative) higher electrophoretic mobility.

Both of the foregoing protocols are based on the use of some type of gel material as the separating medium. In slab-gel electrophoresis, the sample is placed upon a suitable electrophoretic medium (e.g., paper, cellulose acetate membranes, agarose, etc.). The medium is electrophoresed at a suitable voltage to cause separation of the variants; the electrophorsized gels are then fixed and stained. This procedure is somewhat complex, requires skill, and can require up to about one hour to obtain clinically useful results. Examples of well recognized and widely accepted types of slab gel electrophoretic protocols are the PARAGON ® slab gel electrophoretic system and APPRAISE ® densitometer electrophoresis systems (available from Beckman Instruments, Inc., Fullerton, Calif. USA). For slab gel electrophoretic separations of hemoglobin variants, Hemoglobin A, Hemoglobin F, Hemoglobin S and Hemoglobin C have been separated using a basic buffer (e.g., a 50 mM barbital buffer, pH 8.6). However, in order to achieve unequivocal separation of Hemoglobin S from co-migrating variants (e.g., Hemoglobins D and G), an acidic buffer must be used (e.g., 70 mM maleate, pH 6.0).

Isoelectric focusing allows for the simultaneous separation of Hemoglobins A, F, S and C. See, e.g., Zhu, M. et al. "Optimizing Separation Parameters in Capillary Isoelectric Focusing." *J. Chrom.* 559:479-488 (1991), which is incorporated herein by reference. However, isoelectric focusing is not a widely accepted methodology for such separations. This technique requires the use of a stable pH gradient such that the hemoglobin variants migrate via electrophoretic techniques to the zone where the pH is equal to the isoelectric point of the variant; in such a zone, the effective charge of the variant becomes zero, and migration ceases. Isoelectric focusing of hemoglobin variants has been applied using capillary electrophoresis techniques whereby a polyacrylamide coated microcapillary column comprising a buffer solution including carrier ampholytes (compounds which are both conductive and provide the necessary pH gradient) is used as the separation medium. Coating of the microcapillary column is essential for isoelectric focusing techniques. After the hemoglobin variants are separated in the various zones, an electrophoretic current is applied, and the separated variants are sequentially detected as they move through the capillary column past a detection system.

While capillary electrophoretic isoelectric focusing poses unique problems, capillary zone electrophoretic techniques are of interest. Capillary zone electrophoresis ("CZE") is a technique which permits rapid and efficient separations of charged substances. Separation of the constituents of clinical samples (i.e. whole blood, plasma, serum, urine, cerebrospinal fluid) can be accomplished in less than 20 minutes, typically in less than 10 minutes. In general, CZE involves introduction of a sample into a capillary tube, i.e. a tube having an internal diameter of from about 2 to about 2000 microns ("$\mu$m"), and the application of an electric field to the tube. The electric potential of the field both pulls the sample through the tube and separates it into its constituent parts. I.e., each of the sample constituents has its own individual electrophoretic mobility; those having greater mobility travel through the capillary tube faster than those with slower mobility. As a results the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel e.g., polyacrylamide gel. Separation of the constituents in the sample is predicated in part by the size and charge of the constituents travelling through the gel matrix. Gel CZE has several disadvantages, notably, the unpredictability of the gel material. I.e., such gels eventually "breakdown" or can only be used for limited analytical runs. Such unpredictability is unacceptable in any setting where numerous analytical runs are conducted.

In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (i.e., the buffer solution and the sample being analyzed), must also flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based electrophoresis.

Fused silica is principally utilized as the material for the capillary tube because it can withstand the relatively high voltage used in CZE, and because the inner walls ionize to create the negative charge which causes the desired electroendosmatic flow. However, alumina, beryllium, Teflon ®-coated materials, glass, and combinations of these (with or without fused silica) can also be utilized. The capillary column is typically capable of withstanding a wide range of applied electrophoretic fields of between about 10 volts per centimeter ("v/cm") up to about 1000 v/cm. The capillary column may be coated on the outside (using, e.g., a polyamide material) for ease of handling. The inner wall of the capillary may be untreated or coated with a material capable of, inter alia, reducing adsorption to the inner wall during electroendosmatic flow of the bulk solution. However, it is typically preferred that the inner wall be uncoated because typical coatings have a tendency to breakdown in an unpredictable manner.

Open CZE has many desirable qualities for clinical sample analysis: because the analysis does not involve a gel-filled column, the inherent limitations on the number of analytical runs that can be conducted with any particular gel-filled column are avoided; when the capillary column is untreated, the aura of unpredictability which can be associated with coated columns is avoided; the sample size is small (usually on the order of 5 to 200 $\mu$l of diluted sample); sample analysis time is fast, i.e. less than about 20 minutes; and the protocol lends itself to automation, thus decreasing the labor skills necessary for efficient and effective sample analysis. Heretofore, the unequivocal separation of hemoglobin variants, and in particular hemoglobin variants A, F, S and C, has not been demonstrated using open CZE protocols.

Given to benefits associated with open CZE, and the necessity for screening for hemoglobin variants, it would be advantageous to have an open tube CZE protocol for analyzing hemoglobin variants.

SUMMARY OF THE INVENTION

The present invention satisfies the above need by providing a capillary zone electrophoresis method for the analysis of hemoglobin and the variants of hemoglobin comprising the steps of:

a) introducing a sample comprising hemoglobin and the variants of hemoglobin into a capillary tube containing therein a buffer, said buffer comprising at least about 100 mM of barbituric acid, the derivatives of barbituric acid, or a combination thereof said buffer having a pH of at least about 8.0;

b) applying an electric field to said capillary tube of sufficient voltage to allow for the separation of hemoglobin and the variants of hemoglobin; and c) detecting said hemoglobin and the variants of hemoglobin. Most preferably, the buffer comprises about 240 mM of barbituric and has a pH of between about 8.5 and about 8.7.

As the hemoglobin and hemoglobin variants are resolved into discrete zones which move past a detection region, the zones can be expressed as e.g., peaks of various widths and heights or numerical values based upon the integrated areas under such peaks. This can in turn be utilized to determine the relative ratios of the hemoglobin and hemoglobin and hemoglobin variants, as well as the concentration of each within the particular sample. Because of the efficiency and speed associated with CZE, numerous samples can be rapidly screened for the presence and identification of hemoglobin variants. Most importantly, the foregoing protocol can be utilized to separate, inter alia, hemoglobins A, F, S and C in a single analytical run without the need for a gel-filled capillary column.

DETAILED DESCRIPTION OF PREFERRED EMBODIMENTS

Figure 1:
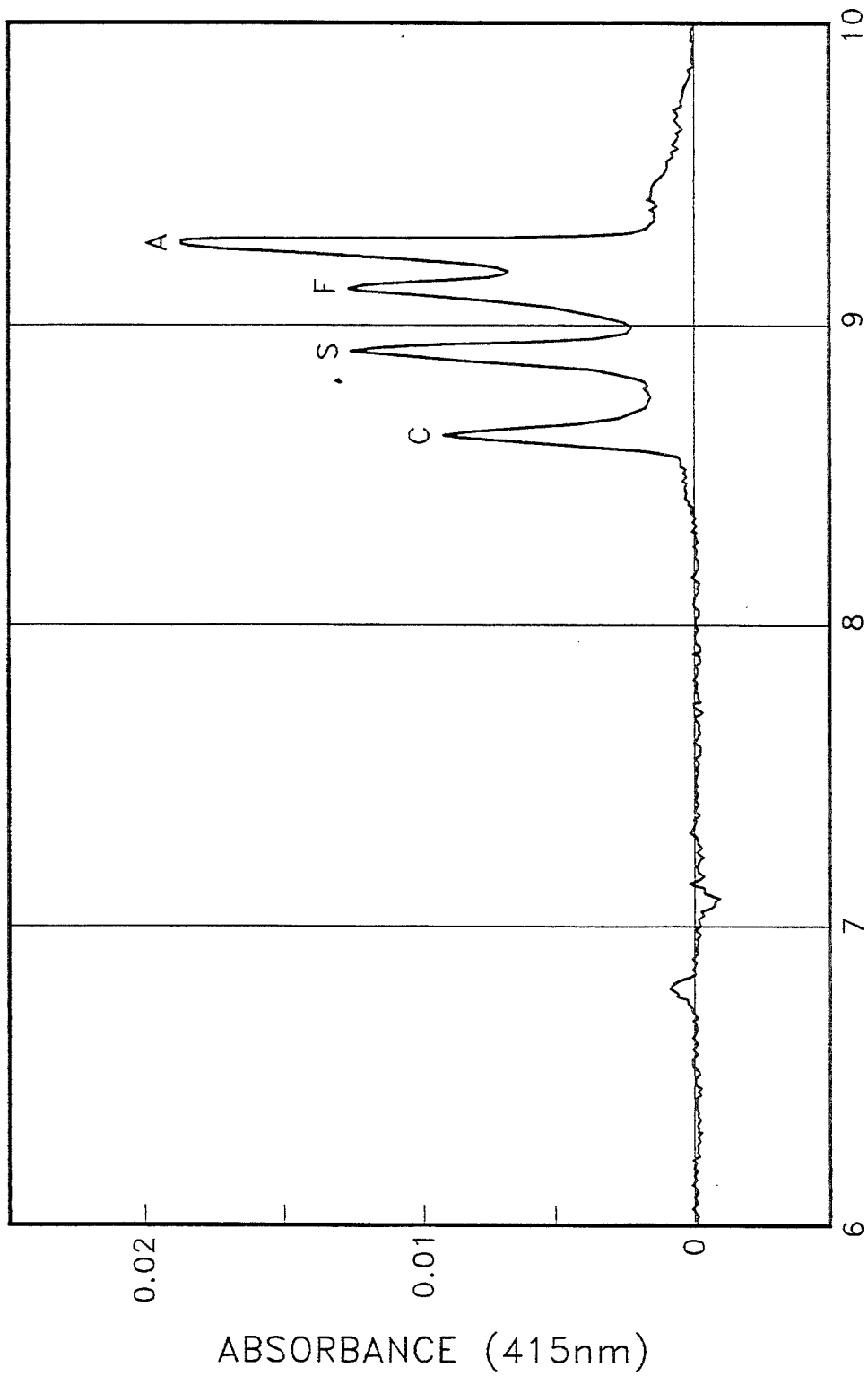
FIG. 1 is an electropherogram of a control sample comprising hemoglobin variants A, F, S, C, using a 240 mM barbital buffer, pH 8.6, by open CZE with an untreated capillary column.

Hemoglobin variants have nearly the same amino acid sequences; the differences in such sequences, leads to the production of such variants. The electrophoretic mobilities of the variants are also very similar. Thus, it is essential that any separation technique be capable of readily and efficiently discriminating such small differences. With respect to CZE techniques, the buffer within the capillary column is relied upon for such discrimination. Applicant has discovered that under specified conditions, a buffer comprising barbituric acid, or the derivatives of barbituric acid, can efficiently discriminate hemoglobin variants in an open CZE system.

While low ionic strength (i.e. between about 50 and 75 mM) barbituric acid has been utilized in the separation of hemoglobin A, hemoglobin F, hemoglobin S and hemoglobin C in slab-gel electrophoresis, heretofore barbituric acid has not evidenced an ability to unequivocally separate Hemoglobins S from other hemoglobin variants. It has been surprisingly discovered, however, that barbituric acid and the derivatives of barbituric acid (e.g., phenobarbital, mephobarbital, barbital, amobarbital, beta barbital, secobarbital, pentobarbital, thiobarbital, etc.) having an ionic strength of greater than at least about 100 mM and a pH of at least about 8.0, efficiently and effectively separates, inter alia, hemoglobins A, F, S and C in an open CZE format. This provides at least two distinct advantages over previous protocols for separation of hemoglobin variants: 1) the clinically significant hemoglobin variants, inter alia, hemoglobin A, F, S and C, can be analyzed using a single sample to achieve separations similar to those achieved using isoelectric focusing techniques; 2) because the analysis can be conducted using an open CZE format using untreated columns, limitations associated with separating gels the aura of unpredictability associated with both gel materials used for filling the columns and, to the degree not utilized, coated capillary columns, are eliminated.

Preferably, barbituric acid is utilized, and most preferably 5,5-diethyl-barbituric acid. Preferably, the ionic strength of the barbituric acid is at least about 100 mM and preferably between about 175 mM and 250 mM. The capillary column need not be coated on the inner wall thereof; it is most preferred that ionic strength of the barbituric acid and derivatives of barbituric acid used in conjunction with such columns be about 240 mM. Coated columns can also be utilized; it is preferred that the ionic strength of the barbituric acid and derivatives of barbituric acid used in conjunction with such coated columns be between about 100 mM and 200 mM. However, irrespective of the condition of the inner wall of the column, the ionic strength of barbituric acid and the derivatives of barbituric acid should be between about 100 mM and about 250 mM.

At pH of about 8.6, all hemoglobin species contain a net negative charge. A net negative charge is necessary for the hemoglobin variants to be separated because under the influence of an electric field, such negatively charge species travel towards a cathode under the influence of the electroendosmatic flow of the bulk solution. Barbituric acid, e.g., has a pH of between about 5.5 and 6.0. Thus, it is necessary to adjust the pH of the barbituric acid upwards to an alkaline value using a pH modifier, i.e., a material capable of adjusting the pH of a solution to a desired value. Preferred pH modifiers include, e.g., alkaline metal salts (sodium, potassium, lithium rubidium, francium) and compounds comprising ammonium ions, i.e. ammonium phosphate and ammonium carbonate. The particular pH modifier is not, in and of itself, of critical import. What is important is that the pH of the buffer be at least about 8.0, preferably between about 8.0 and about 10.0, more preferably between about 8.0 and about 9.0, and most preferably between about 8.5 and about 8.7. A most preferred pH modifier is sodium hydroxide.

As those in the art appreciate, in order to effectively analyze hemoglobin variants, the hemoglobin must first be liberated from red blood cells. Thus, any agent capable of lysing red blood cells (without, of course, damaging the liberated hemoglobin) can be utilized. Such agents are well know and will not be discussed herein in detail. A preferred lysing agent is nonylphenol polyethylene glycol ether; such an agent is commercially available from Beckman Instruments, Inc. (Hemolyzing Reagent, PARAGON® Hemoglobin electrophoresis kit; P/N 441780; comprises 0.4% (w/v) nonylphenol polyethylene glycol ether). An alternative to the foregoing is to first separate the red blood cells from the whole blood sample (via, e.g., centrifugation), and lyse the separated red blood cells. This procedure beneficially removes, e.g., serum proteins from the sample to be analyzed.

A normal concentration of hemoglobin in a clinical sample is about 60 mg/ml; such a concentration is typically too high to be analyzed via capillary electrophoretic techniques, principally because of sample overloading in the capillary. Accordingly, it is preferred that the sample be diluted prior to analysis. Preferably, the concentration of the hemoglobin in the sample to be analyzed is less than about 15.0 mg/ml, preferably less than about 7.0 mg/ml, and most preferably about 2.0 mg/ml. Applicable diluents are also well known in the art and will not be discussed herein in detail. Preferably, the diluent has a neutral pH; phosphate buffered saline is an exemplary diluent.

A most preferred embodiment of the disclosed hemoglobin variant buffer comprises the following ingredients:

| Constituent | Formula Weight | g/100 mL* | mM |
| --- | --- | --- | --- |
| 5,5-Diethyl barbituric acid | 184.19 | 4.12 | 200.0 |
| 5,5-Diethylbarbituric acid sodium salt | 206.19 | 0.74 | 40.0 |
| Total | | 4.86 | | pH: 8.6 ± 0.1
*(deionized water)

EXAMPLES

The following examples directed to preferred embodiments of the invention disclosed herein are not intended, nor should they be construed, as limiting the disclosure, or the claims to follow:

I. MATERIALS AND METHODS

A. Capillary Electrophoresis Procedures

Capillary electrophoresis of samples was performed on a Beckman Instruments, Inc. high performance capillary electrophoresis system (Beckman Instruments, Inc., Fullerton, Calif. USA, Model No. 357573). Data analysis was performed on System Gold ™ software (Beckman Instruments, Inc.). The aforementioned capillary electrophoresis system contains built-in 200, 206, 214, 280, 240 and 415 nm narrow-band filters for on-line detection. Electrophoresis was performed using uncoated fused silica tubes having 75 µm internal diameter ("i.d."), 25 cm long; 25 µm i.d., 35 cm long; and 50 µm i.d., 25 cm long (Polymicro Technologies, Phoenix, Ariz. Product Nos. TSP-075335, TSP-025375 and TSP-050375, respectively). The detection window was located approximately 6.5 cm from the column outlet. A coated capillary column having a 50 µm i.d., 25 cm long (Supelco, Bellefonte, Pa. 16823 USA; Product No. CElect-P150 7-5001) was also utilized. Prior to the analysis, the columns were filled with the Hemoglobin Variant Buffer.

Samples were placed on the inlet tray of the above referred capillary electrophoretic system. Samples can be injected into the column by several methods, including, e.g., electrokinetic injection, pressure injection, etc. These protocols are understood by those in the art. For the Examples, the sample was introduced using the electrokinetic method by applying 1.0 kV to the column for about 3–10 seconds. Hemoglobin variants were separated using a column voltage gradient of 200 V/cm (current:140 µA) for the columns having a 75 µm i.d.; 450 V/cm (current:34 µA) for the columns having a 25 µm i.d.; 200 V/cm (current:86 µA) for the columns having a 50 µm i.d., and 200 V/cm (current:42 µA) for the coated columns having a 50 µM i.d. using 100 mM barbituric buffer.

For the analyses, hemoglobin variants were detected at 415 nm. Analyses was conducted at ambient temperature (25° C.). The capillary columns were washed and reconditioned between each run using 1N NaOH for 2 minutes followed by deionized water for 30 seconds.

B. Comparative Slab-Gel Analyses

A comparative analysis was conducted by an agarose slab-gel electrophoresis method using a Beckman Instruments, Inc. PARAGON® electrophoresis system (Product No. 441780). For analysis of Hemoglobin variants A, C and S, the "Acid-Hb gel" portion of the aforementioned system was utilized. Testing was conducted in accordance with manufacturer instructions.

C. Hemoglobin Variant Controls

Two hemoglobin variant controls were utilized. The first consisted of Hemoglobins A, C and S and was obtained from Beckman Instruments, Inc. (I.-D. Zone® Hemoglobin AF/ASC electrophoresis kit, Product No. 667630). The second consisted of Hemoglobins A, F, C and S and was obtained from Isolab, Inc., Akron, Ohio (Product No. HEC-800).

Samples were diluted 1 part sample to 10 parts ICS ™ Diluent (Beckman Instruments, Inc., Product No. 663630). The diluent comprises phosphate buffered saline, pH 7.0. Such dilution ratio provided a hemoglobin concentration of between about 2.0 and about 5.0 mg/ml.

D. Hemoglobin Variant Patient Sample

Packed red cells obtained from a Hemoglobin C heterozygote patient (UCLA Harbor General Hospital) was prepared by admixing therewith in a 1:4 dilution ratio Beckman Hemolyzing Reagent. Thereafter, this admixture was diluted in a 1:5 dilution ratio with Beckman ICS ™ diluent. Final hemoglobin concentration was between about 2.0 and about 3.0 mg/ml.

E. Hemoglobin Variant Buffers

Hemoglobin variant buffers were prepared by admixing 5,5-diethylbariituric acid with deionized water to achieve ionic strengths of 100, 200 and 240 mM. 1.0N sodium hydroxide was used to adjust the pH of the buffers to 8.6+/−0.1. As the solubility of the buffer is somewhat "sluggish" at pH 8.6, the deionized water can be warmed slightly prior to admixing with the 5,5-diethybarbituric acid. All buffers were filtered through a 0.45 µm (pore size) filter before use.

II. EXAMPLE I

ANALYSIS OF HEMOGLOBIN VARIANTS A, C, S AND F

Analysis of Hemoglobin variants A, F, S and C controls was conducted using 240 mM barbital buffer, pH 8.6, using an untreated 75 μm i.d. capillary column. FIG. 1 evidences that excellent separation of the variants was achieved in less than 10 minutes.

The results indicate, inter alia, that these variants can all be separated in a single analytical run in an open-tube CZE form using the disclosed buffer.

II. EXAMPLE II

ANALYSIS OF HEMOGLOBIN VARIANTS A, C AND S

Figure 2:
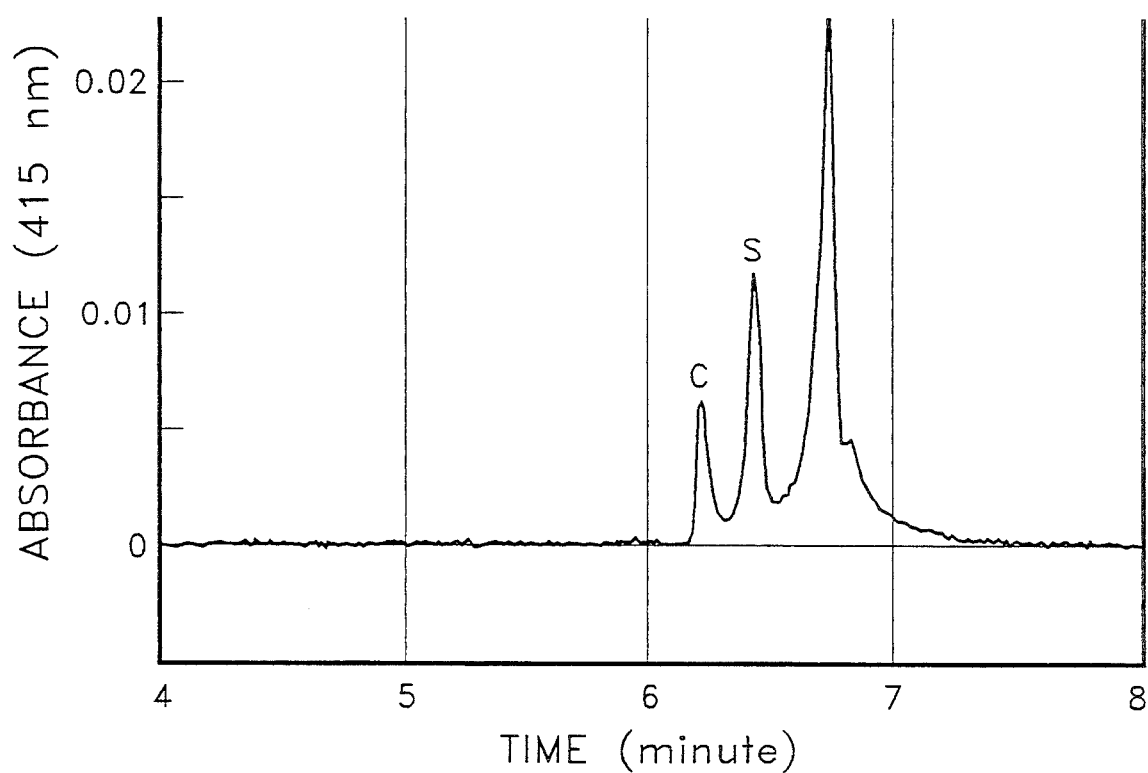
FIG. 2 is an electropherogram of a control sample comprising hemoglobin variants A, S and C using the conditions described for FIG. 1.

Analysis of Hemoglobin variants A, C and S controls was conducted using 240 mM barbital buffer, pH 8.6, using an untreated 25 μm i.d. capillary column. FIG. 2 evidences that excellent separation of the variants was achieved in less than 7 minutes.

III. EXAMPLE III

COMPARATIVE ANALYSIS OF HEMOGLOBIN VARIANTS A, C AND S

Figure 3:
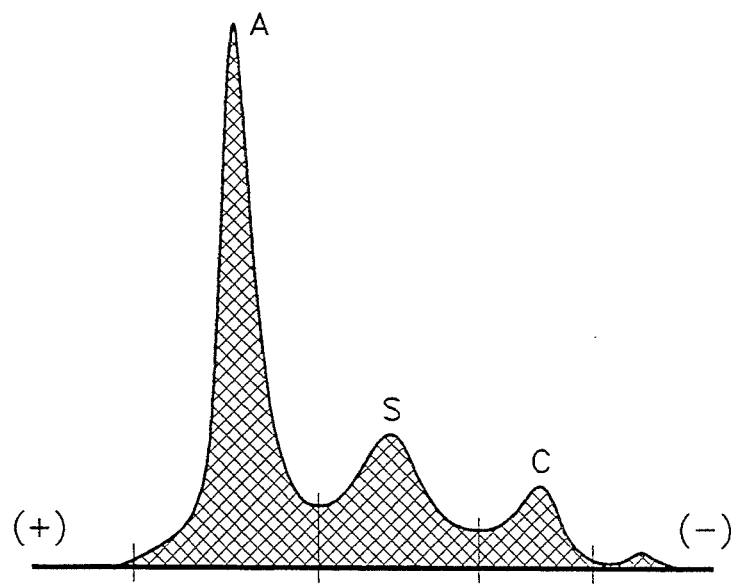
FIG. 3 is a densitometer reading of the same sample used in FIG. 2 as derived by the acid-Hb PARAGON® gel electrophoresis system.

The Hemoglobin variants A, C and S were analyzed using the aforementioned PARAGON® and APPRAISE® systems. Results are presented in FIG. 3. Note that the relative peak heights are approximately the same for the corresponding variants of FIGS. 2 and 3 (as is appreciated by those in the art, CZE electropherograms represent a "first-in-last-art" arrangement—this is why the peak for the Hemoglobin A variant appears last from a left-to-right perspective).

IV. EXAMPLE IV

ANALYSIS OF HEMOGLOBIN VARIANTS A, S AND C

Figure 4:
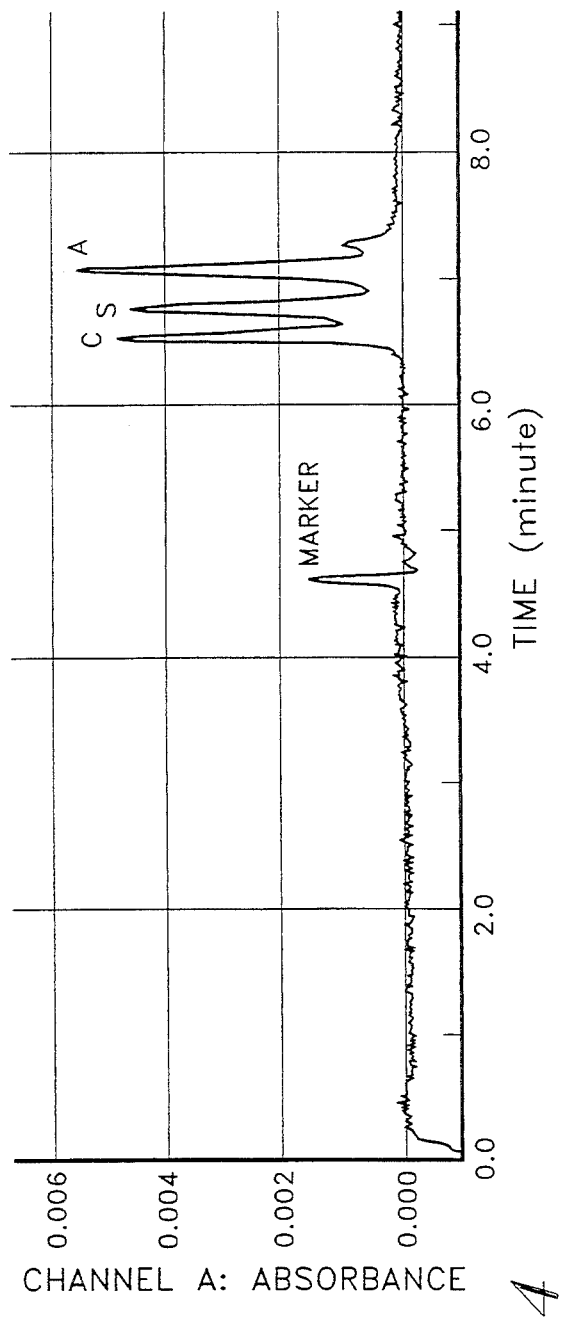
FIG. 4 is an electropherogram of a control sample comprising hemoglobin variants A, S and C using 200 mM barbital buffer, pH 8.6, by open tube CZE with a commercially available coated-capillary column.

Analysis of Hemoglobin variants A, C and S controls was conducted using 200 mM barbital buffer, pH 8.6, using a 50 μm i.d. Supelco coated capillary column. FIG. 4 evidences the excellent separation of the variants was achieved in less than about 8 minutes.

V. EXAMPLE V

ANALYSIS OF HEMOGLOBIN C HETEROZYGOTE PATIENT SAMPLE

Figure 5:
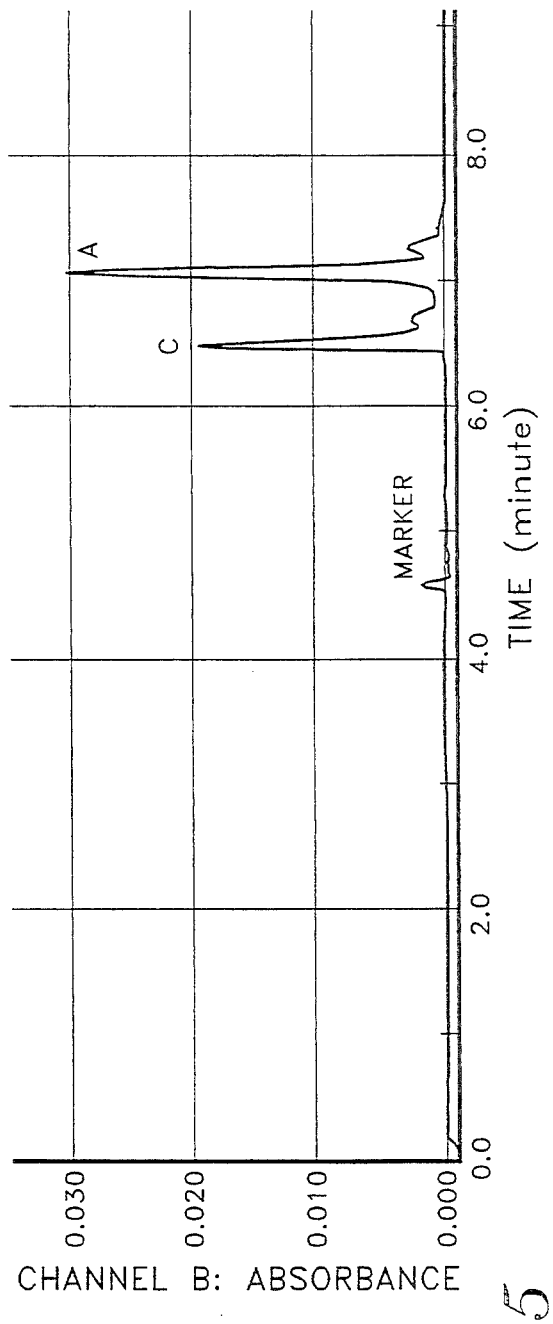
FIG. 5 is an electropherogram of a hemoglobin C heterozygote patient sample using 200 mM barbital buffer, pH 8.6, by open tube CZE with an untreated capillary column.

Analysis of a sample from a Hemoglobin C heterozygote patient was conducted using 200 mM barbital buffer, pH 8.6, using a 50 μm i.d. capillary column. As evidenced by the electropherogram of FIG. 5, excellent separation of the Hemoglobin C variant from Hemoglobin A was achieved in less than about 8 minutes.

VI. EXAMPLE VI

ANALYSIS OF HEMOGLOBIN VARIANTS A, S AND C

Figure 6:
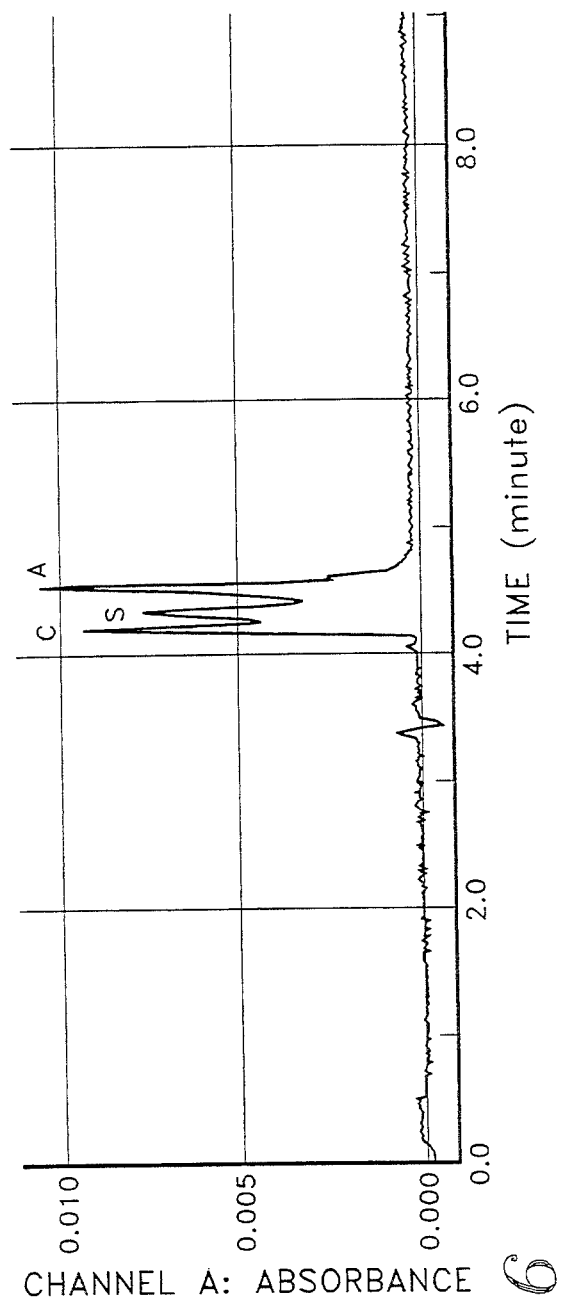
FIG. 6 is an electropherogram of a control sample comprising hemoglobin variants A, S and C using 100 mM barbital buffer, pH 8.6, by open tube CZE with a commercially available coated capillary column.

Analysis of Hemoglobin variants A, C and S controls was conducted using 100 mM barbital buffer, pH 8.6, using 50 μm i.d. Supelco coated capillary column. FIG. 6 evidences that excellent separation of the variants was achieved in less than about 5 minutes.

VII. EXAMPLE VII

ANALYSIS OF HEMOGLOBIN C HETEROZYGOTE PATIENT SAMPLE

Figure 7:
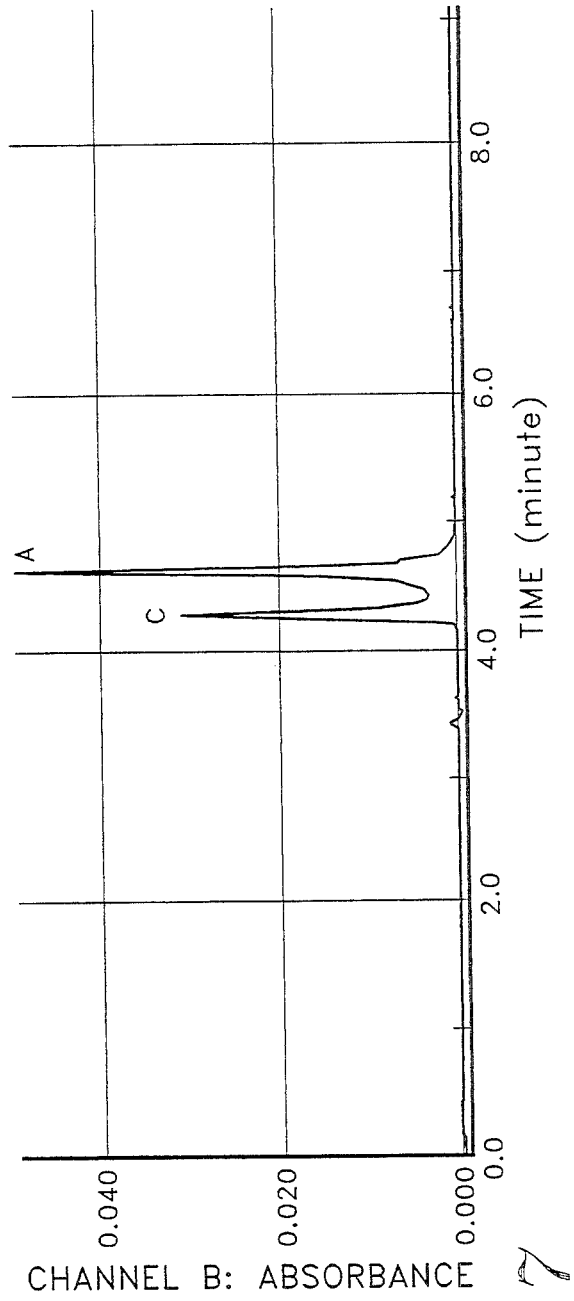
FIG. 7 is an electropherogram of the patient sample of FIG. 5 using the conditions of FIG. 6.

Analysis of a sample from a Hemoglobin C heterozygote patient was conducted using 100 mM barbital buffer, pH 8.6, using a 50 μm i.d. Supelco coated capillary column. As is evident from FIG. 7, excellent separation of the Hemoglobin C variant was achieved in less than about 5 minutes.

The foregoing data demonstrates that hemoglobin and the variants of hemoglobin can be analyzed in a CZE format utilizing the methodology described herein. It is to be understood that the foregoing Examples are not to be construed as limiting the invention. The disclosed methodology is not limited to the specific high performance capillary electrophoresis system utilized herein. For example, laser-induced fluorescence based systems can be utilized. Furthermore, the methodology is not to be construed as limited to analysis of clinical samples in that the methodology has broader applications to non-clinical samples comprising hemoglobin and/or hemoglobin variants, e.g., control samples, non-human samples, etc. It is to be further understood that the foregoing methodology can also be utilized to determine, inter alia, the concentration of hemoglobin and hemoglobin variants in a sample, as well as the relative proportions thereof in such sample, utilizing techniques known in the art. As such, the foregoing Detailed Description of Examples are not intended, nor are they to be construed, on a limitation on the disclosed methodology or the claims to follow. Modifications and equivalents which are within the purview of the skilled artisan are considered to be included within the scope of the invention or claimed. By way of example, introducing an aliquot of a sample and the disclosed buffer as a single mixture into a capillary tube is considered to be equivalent to the introduction of the sample into a capillary tube comprising the buffer.

What is claimed is:

1. A buffer for the analysis of hemoglobin and the variants of hemoglobin by capillary zone electrophoresis comprising:
    (a) between about 175 mM and about 250 mM of a compound selected from the group consisting of:
        i) barbituric acid;
        ii) derivatives of barbituric acid;
        iii) combinations of barbituric acid and the derivatives of barbituric acid; and
        iv) combinations of the derivatives of barbituric acid,
    (b) at least one hemoglobin variant selected from the group consisting of hemoglobin A, hemoglobin F, hemoglobin S and hemoglobin C;
   wherein the pH of said buffer is at least about 8.0.

2. The buffer of claim 1 wherein said compound is selected from the group consisting of 5,5-diethyl barbituric acid, phenobarbital, mephobarbital, barbital, amobarbital, beta barbital, secobarbital, pentobarbital, and thiobarbital.

3. The buffer of claim 1 wherein said compound is 5,5-diethyl barbituric acid.

4. The buffer of claim 1 wherein the ionic strength of said compound is about 240 mM.

5. The buffer of claim 1 wherein the pH of said buffer is between about 8.0 and about 10.0.

6. The buffer of claim 1 wherein the pH of said buffer is between about 8.0 and about 9.0.

7. The buffer of claim 1 wherein the pH of said buffer is between about 8.5 and about 8.7.

8. The buffer of claim 1 wherein said buffer further comprises at least one pH modifier.

* * * * *